US010106506B2

(12) United States Patent
Dong et al.

(10) Patent No.: US 10,106,506 B2
(45) Date of Patent: Oct. 23, 2018

(54) GENERAL PROCESS FOR THE PREPARATION OF 6-SUBSTITUTED OR 5,6-DISUBSTITUTED DERIVATIVES OF 2-AMINO-ISONICOTINIC ACID

(71) Applicant: Boehringer Ingelheim International GmbH, Ingelheim am Rhein (DE)

(72) Inventors: Weitong Dong, Shanghai (CN); Da Deng, Shanghai (CN); Yan Fu, Shanghai (CN); Xiangle Jin, Shanghai (CN); Lidong Xing, Shanghai (CN); Jun Yan, Shanghai (CN)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/738,632

(22) PCT Filed: Jul. 1, 2016

(86) PCT No.: PCT/EP2016/065535
§ 371 (c)(1),
(2) Date: Dec. 21, 2017

(87) PCT Pub. No.: WO2017/001670
PCT Pub. Date: Jan. 5, 2017

(65) Prior Publication Data
US 2018/0186741 A1    Jul. 5, 2018

(30) Foreign Application Priority Data

Jul. 2, 2015 (WO) ................ PCT/CN2015/083149

(51) Int. Cl.
*C07D 213/12* (2006.01)
*C07D 213/803* (2006.01)
*C07D 213/80* (2006.01)

(52) U.S. Cl.
CPC ....... *C07D 213/803* (2013.01); *C07D 213/80* (2013.01)

(58) Field of Classification Search
CPC ........................... C07D 213/80; C07D 213/83
USPC ...................................................... 546/250
See application file for complete search history.

(56) References Cited

U.S. PATENT DOCUMENTS

2011/0092544 A1* 4/2011 Finkelstein .......... C07D 213/24
514/334

FOREIGN PATENT DOCUMENTS

WO   2008033745 A2   3/2008
WO   WO2013072882  *  5/2013

OTHER PUBLICATIONS

Casimiro-Garcia; J. Med. Chem. 2011, 54, 4219-4233. (Year: 2011).*
Kobayashi; Chem. Pharm. Bull. 1995, 43, 788-796. (Year: 1995).*
Katsujiro et al., "Studies on the syntheses of vitamin B6 derivatives. Synthesis of 2-aminonicotinic acid derivatives", Journal of the Pharmaceutical society of Japan, 1962, vol. 82, No. 4, pp. 532-535.

(Continued)

*Primary Examiner* — Daniel R Carcanague
(74) *Attorney, Agent, or Firm* — Philip I. Datlow

(57) ABSTRACT

This invention relates to a novel synthetic method for the preparation of 6-substituted or 5,6-disubstituted derivatives of 2-amino-isonicotinic acid.

13 Claims, 1 Drawing Sheet

X-ray structure of Compound 3

(56) References Cited

OTHER PUBLICATIONS

Smirnova et al., "Synthesis and reations of esters of 3-cyano-2-oxo-5,6-tri(tetra)methylene-1,2-dihydroisonicotinic and 2-amino-3-ethoxycarbonyl-5,6-tri(tetra)-methyleneisonicotinic acids", Chemistry of heterocyclic compounds, vol. 2, No. 12, 1996'-1996, pp. 319-322.
International Search Report and Written Opinion for corresponding application, PCT/EP2016/065535, dated Oct. 31, 2016.

* cited by examiner

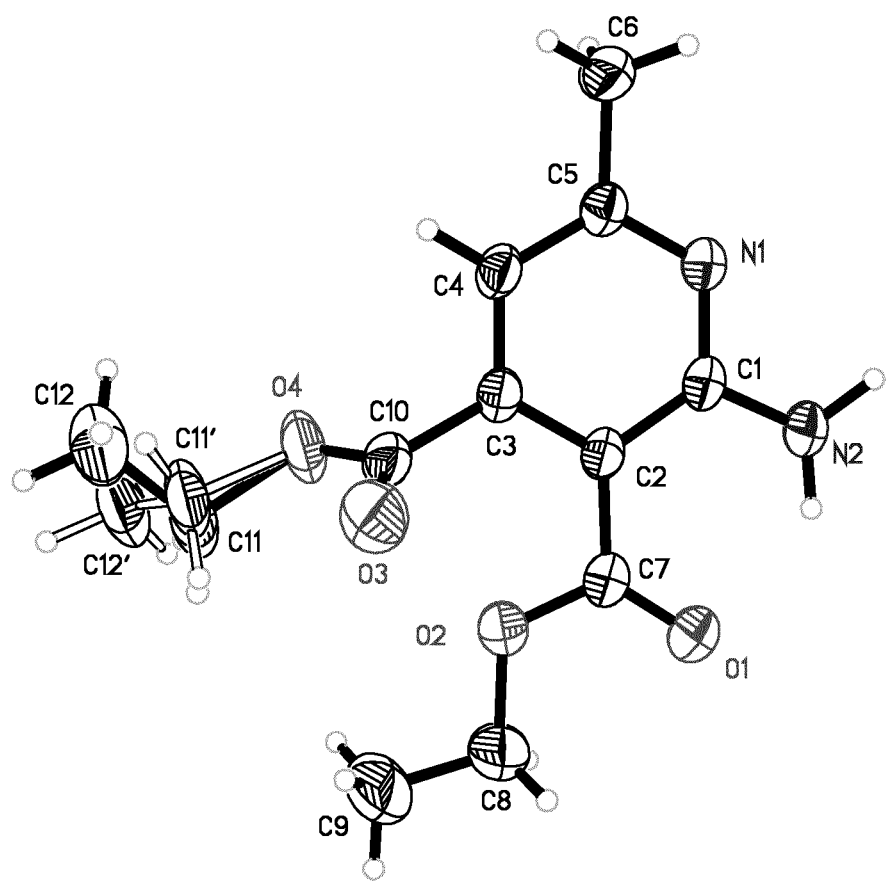
X-ray structure of Compound 3

GENERAL PROCESS FOR THE PREPARATION OF 6-SUBSTITUTED OR 5,6-DISUBSTITUTED DERIVATIVES OF 2-AMINO-ISONICOTINIC ACID

FIELD OF THE INVENTION

This invention relates to a novel synthetic method for the preparation of 6-substituted or 5,6-disubstituted derivatives of 2-amino-isonicotinic acid.

BACKGROUND 6-substituted or 5,6-disubstituted derivatives of 2-amino-isonicotinic acid, e.g. 6-methyl-2-amino-isonicotinic acid and its methyl ester or N,N-dimethyl amide (WO 2010115836, WO 2012045803 and WO 2013149926), are important intermediates in the manufacture of pharmaceutically active ingredients.

The known chemical syntheses of 2-amino-pyridines offer only limited access to 6-substituted or 5,6-disubstituted derivatives of 2-amino-isonicotinic acid and all face severe drawbacks that do not allow for supply of these important intermediates at larger or industrial scale. Therefore, there has been a need to develop a novel approach to these compounds. The present invention provides a simple and selective approach to these intermediates which in addition is scalable.

Up to date, the following methods for the preparation of 2-amino-pyridines have been described:

One of the most widely used amination methods for construction of 2-aminopyridine moiety is substitution of 2-halopyridines and analogues with ammonia or an equivalent under high temperature (150-250° C.) and pressure, or under palladium or copper catalyzed conditions with involvement of sealed autoclave or tube. These conditions limit the use of this protocol at large or industrial scale.

6-methyl-2-amino-isonicotinic acid can be prepared in moderate yield by converting 6-methyl-2-chloro-isonicotinic acid into 6-methyl-2-amino-isonicotinic acid under high pressure and high temperature in an autoclave (WO 2012045803 and SCHEME 1). The disadvantages are high pressure, high temperature and use of an autoclave.

SCHEME 1

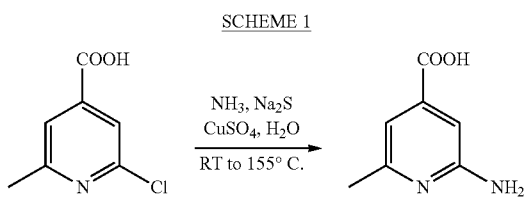

Although the Chichibabin Reaction gives 2-aminopyridines directly from pyridines, it is rarely used in industrial scope because of low yields and poor functional group tolerance.

Another synthetic approach to 2-aminopyridines employs pyridine-N-oxides (SCHEME 2). Treatment of pyridine-N-oxides with activating agents enhances the electrophilic character of the 2-position, thus allowing for nucleophilic addition of ammonia (Org. Lett., 2010, 12, 5254-5257) or its equivalent (like tert-butylamine, J. Org. Chem., 2007, 72, 4554-4557). Disadvantages of this approach are that pyridines have to be converted to the corresponding pyridine-N-oxides constituting an additional synthesis step and that 4-amino-pyridines are formed as side products.

SCHEME 2

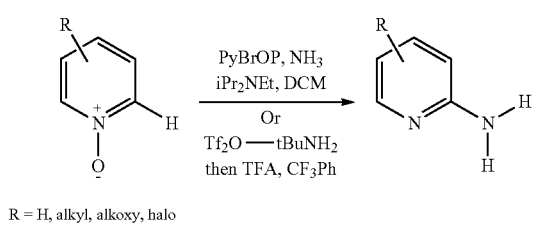

R = H, alkyl, alkoxy, halo

Another method is to construct the 2-aminopyridine moiety using 1,3-dione derivatives or equivalents and 3-amino-3-imino-propanoic ester or amide (Heterocycles, 1976, 5, 255-260; Tetrahedron Lett., 1994, 35, 5775-5778; WO 2006059103; Tetrahedron, 2007, 63, 4491-4496). However, this method has only been applied to the synthesis of 4-,6-alkyl substituted nicotinic acid derivatives and not to the synthesis of 2-amino-isonicotinic acid derivatives (SCHEME 3).

SCHEME 3

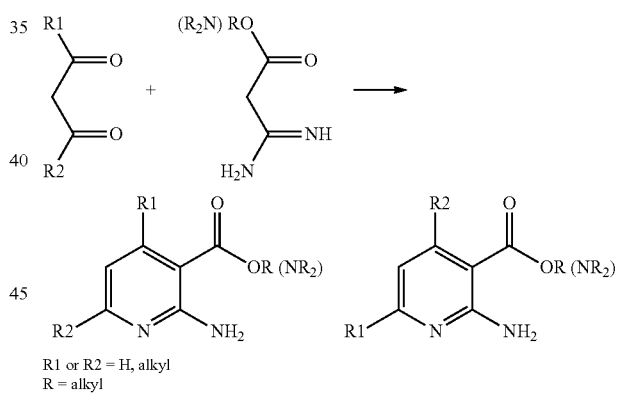

R1 or R2 = H, alkyl
R = alkyl

The present invention provides a general process for the preparation of 6-substituted or 5,6-disubstituted derivatives of 2-amino-isonicotinic acid that overcomes the disadvantages of these methods known in the prior art.

The process according to the present invention does not require the use of ammonia or equivalents, high temperature or high pressure and selectively delivers 6-substituted or 5,6-disubstituted derivatives of 2-amino-isonicotinic acid in a short reaction sequence with good yields and without transition metal wastes.

DESCRIPTION OF THE INVENTION

The present invention provides a novel process for preparing 2-amino-isonicotinic acid derivatives of formula I

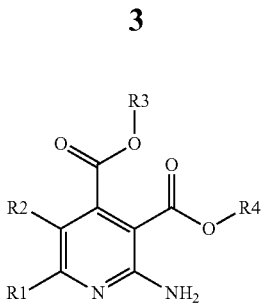

in which
R1 is $C_1$-$C_6$-alkyl- or $C_6$-$C_{10}$-aryl-;
R2 is H—, $C_1$-$C_6$-alkyl- or $C_6$-$C_{10}$-aryl-;
or
R1 and R2 together form a $C_2$-$C_5$-alkyl-group such that a ring is formed;
R3 is $C_1$-$C_4$-alkyl-;
R4 is $C_1$-$C_4$-alkyl-;
comprising the reaction of compound (1)

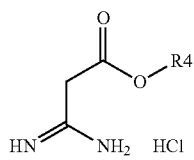

with a compound of formula II

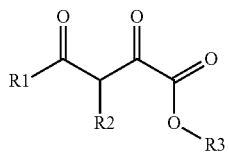

in which R1, R2, R3 and R4 have the meaning as in formula I,
in which water is eliminated (condensation reaction).

In a second embodiment, the process according to the first embodiment above is characterized in that
the condensation reaction is followed by hydrolysis of the ester groups —COOR3 and —COOR4 to give intermediate compound of formula III

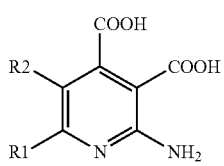

in which R1 and R2 have the meaning as in formula I.

In a third embodiment, the process according to the second embodiment is characterized in that intermediate compound of formula III is reacted under conditions facilitating decarboxylation to give a compound of formula IV

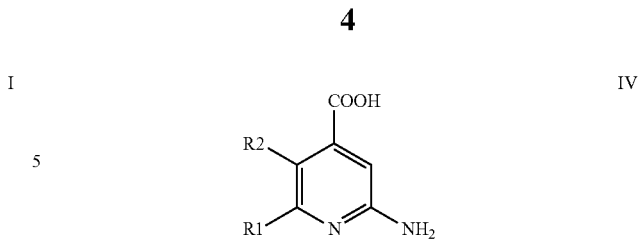

in which R1 and R2 have the meaning as in formula I.

In another embodiment the invention comprises the process according to the first embodiment above, in which R3 and R4 are identical.

In another embodiment, the invention comprises the process according to the first embodiment above
in which
R1 is methyl-, ethyl-, iso-propyl-, tert-butyl- or phenyl-;
R2 is H— or methyl-;
or
R1 and R2 together form a —$CH_2$—$CH_2$—$CH_2$— or —$CH_2$—$CH_2$—$CH_2$—$CH_2$— group such that a ring is formed;
R3 is ethyl- or methyl-;
R4 is ethyl- or methyl-.

In another embodiment, the process according to the first embodiment above
in which
R1 is methyl-, ethyl-, iso-propyl-, tert-butyl- or phenyl- and R2 is H—;
or
R1 is ethyl- and R2 is methyl-;
or
R1 and R2 together form a —$CH_2$—$CH_2$—$CH_2$— group such that a ring is formed;
R3 is ethyl-;
R4 is ethyl-.

In another embodiment the process according to the first embodiment above is characterized in that NaOEt or NaOR3 in R3OH is used in the condensation reaction.

In another embodiment the process according to the first embodiment above is characterized in that the condensation reaction comprises conditions that facilitate elimination of water.

In another embodiment, the process according to the first embodiment above is characterized in that NaOEt in EtOH is used in the condensation reaction.

In another embodiment, the process according to the second embodiment above is characterized in that an inorganic base is used for hydrolysis of the ester groups.

In another embodiment, the process according to the second embodiment above is characterized in that NaOH, LiOH, KOH or Ba(OH)$_2$ is used for hydrolysis of the ester groups.

In another embodiment, the process according to any of the embodiments above is characterized in that the reaction mixture is adjusted to pH=5-6 with an acid after hydrolysis of the ester groups.

In another embodiment, the process according to any of the embodiments above is characterized in that the reaction mixture is adjusted to pH=5-6 with hydrochloric acid or $H_2SO_4$ after hydrolysis of the ester groups.

In another embodiment, the process according to the third embodiment above is characterized in that concentrated $H_2SO_4$ is used for decarboxylation.

In another embodiment, the process according to any of the embodiments above is characterized in that decarboxylation is conducted in the presence of LiCl, NaCl or MgCl$_2$.

In another embodiment, the process according to any of the embodiments above is characterized in that decarboxylation is conducted at a temperature of 120 to 150° C.

In another embodiment, the invention relates to a compound selected from the group of

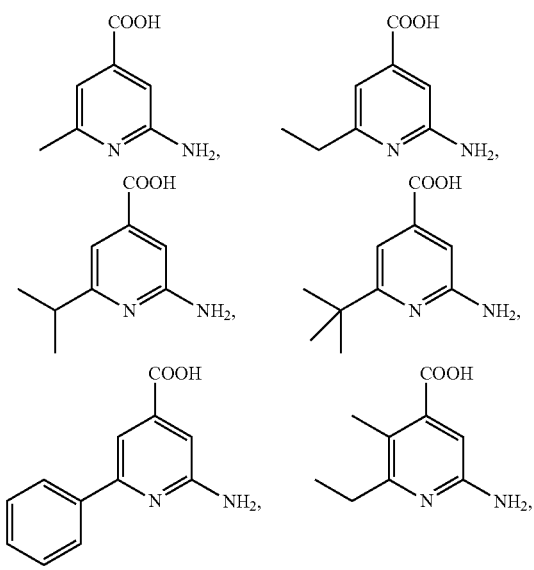

and

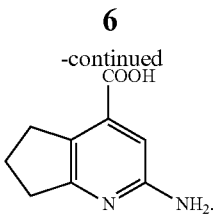

In another embodiment, the invention relates to a compound selected from the group of

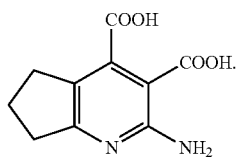

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, tetrahydronaphthyl and dihydronaphthyl.

The present invention provides a general process for the preparation of 6-substituted or 5,6-disubstituted derivatives of 2-amino-isonicotinic acid (SCHEME 4).

SCHEME 4

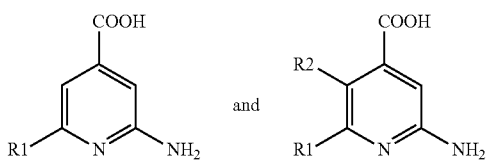

3-Amino-3-imino-propanoic ethyl ester hydrochloride salt (la) is reacted with 2,4-dioxo-pentanoic acid ethyl ester (2) under basic and refluxing conditions (SCHEME 5). Unexpectedly, only one product—surprisingly 2-amino-6-methyl-pyridine-3,4-dicarboxylic acid diethyl ester (3)—has been formed under these conditions. The structure of 2-amino-6-methyl-pyridine-3,4-dicarboxylic acid diethyl ester (3) has been unambiguously determined by a single-crystal X-ray diffraction analysis.

Further reduction of the number of reaction steps has been possible by telescoping the intermediate (3) to the next hydrolysis step for purification. After work-up, 2-amino-6-methyl-pyridine-3,4-dicarboxylic acid (4) is isolated.

Decarboxylation at 3-position occurs easily in case of 2-hydroxy-pyridines (2-pyridones; CN 103086962, CN 102993088). However, very high temperatures (>250° C.) are required for 3-decarboxylation of 2-amino-pyridines (WO 2012101239, WO 2014016434).

Unexpectedly, decarboxylation of 4 occurs under acidic condition (sulfuric acid) in the presence of lithium chloride, magnesium chloride or sodium chloride in NMP already at 130° C. to yield 2-amino-6-methyl-isonicotinic acid (5).

Compound 5 can be converted to its methyl ester (6, overall yield 48%, SCHEME 5) or N,N-dimethyl amide (7, overall yield 40%, SCHEME 6) respectively in high purity.

SCHEME 5

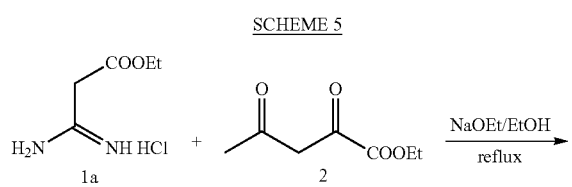

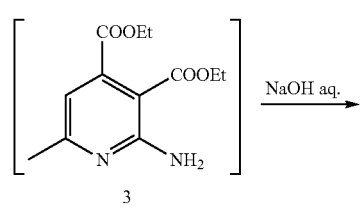

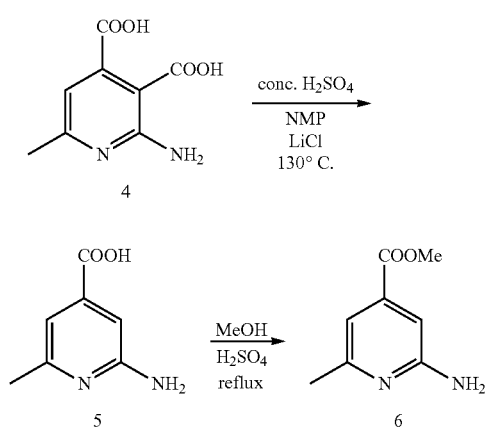

SCHEME 6

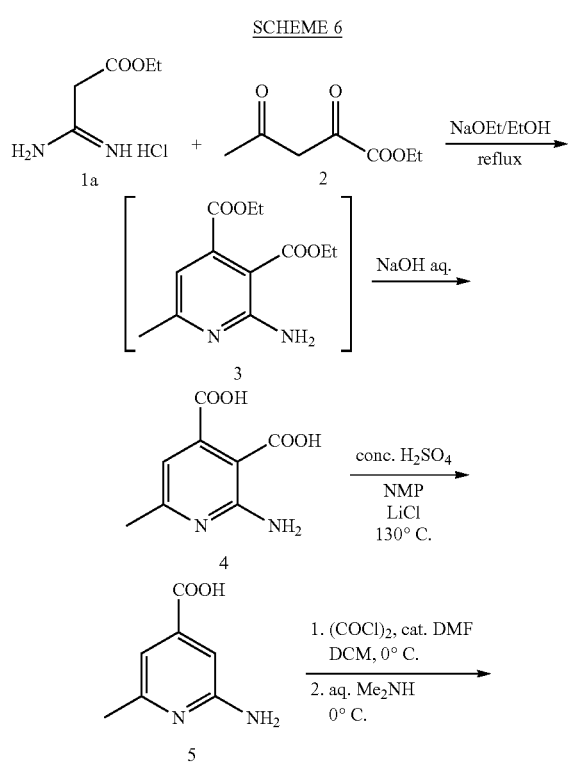

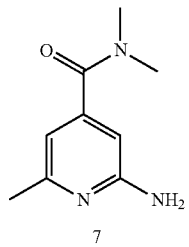

This protocol can be applied to the reaction of 2,4-dioxo-caboxylic acid ethyl esters (8a-8a) with amino-3-imino-propanoic ethyl ester hydrochloride salt (1a, SCHEME 7).

SCHEME 7

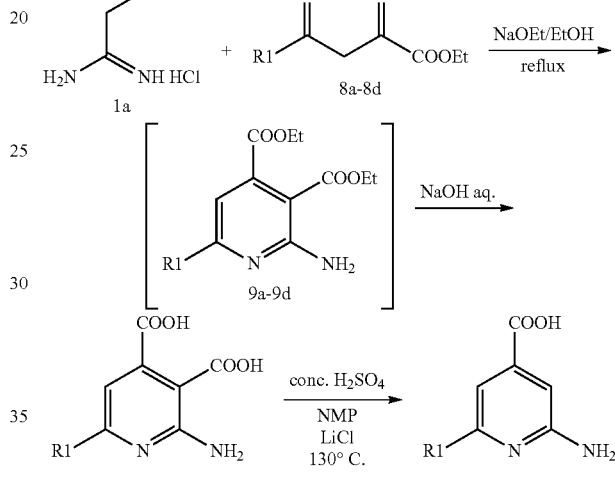

a: R1 = Et, overall yield 71%
b: R1 = i-Pr, overall yield 70%
c: R1 = t-Bu, overall yield 59%
d: R1 = Ph, overall yield 66%

When this protocol is used for the synthesis of 5,6-disubstituted 2-amino-isonicotinic acids starting from compound 12a or 12b, corresponding results are obtained (SCHEME 8). Therefore, this process can be used as a general method to prepare both 6-substituted and 5,6-disubstituted 2-amino-isonicotinic acids, including annelated ring systems.

SCHEME 8

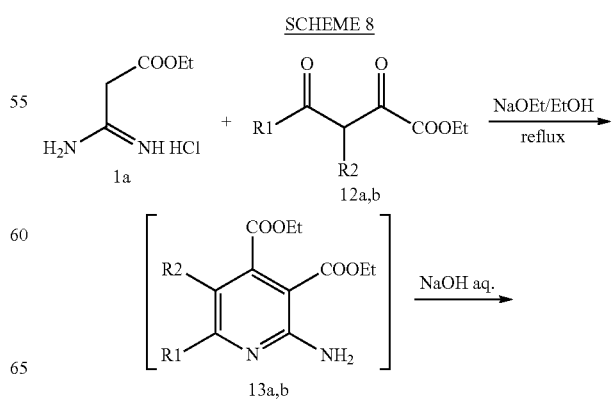

-continued

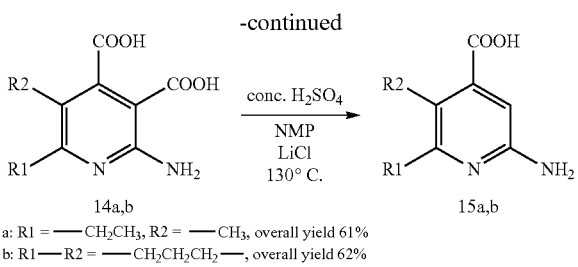

a: R1 = —CH$_2$CH$_3$, R2 = —CH$_3$, overall yield 61%
b: R1—R2 = —CH$_2$CH$_2$CH$_2$—, overall yield 62%

LIST OF ABBREVIATIONS

δ Chemical Shift
$^{13}$C Carbon 13
CF$_3$Ph Trifluoromethylphenyl
(COCl)$_2$ Oxalyl Chloride
CuSO$_4$ Copper Sulfate
d Doublet
D$_2$O Deuterium Water
DCM Dichloromethane
deg degree
DMF N,N-Dimethylformamide
DMSO-d$_6$ Deuterium Dimethyl Sulfoxide
EtOH Ethanol
$^1$H Proton
H$_2$O Water
H$_2$SO$_4$ Sulfuric Acid
HCl Hydrochloric Acid
iPr$_2$NEt N,N-Diisopropyl Ethylamine
LiCl Lithium Chloride
LiCl.H$_2$O Lithium Chloride Monohydrate
m Multiple
m/z Mass-to-Charge Ratio
Me$_2$NH Dimethylamine
MeOH Methanol
MHz Mega Hertz
MS Mass Spectroscopy
Na$_2$S Sodium Sulfide
NaOD Deuterium Sodium Hydroxide
NaOEt Sodium Ethoxide
NaOH Sodium Hydroxide
NH$_3$ Ammonia
NMP N-Methylpyrrolidinone
NMR Nuclear Magnetic Resonance Spectroscopy
PyBrOP Bromo-trispyrrolidino-phosphonium Hexafluorophosphate
q Quartet
RT Room Temperature
s Singlet
t Triplet
Tf$_2$O Trifluoromethylsulfonic Anhydride
TMS Tetramethylsilane

DESCRIPTION OF THE FIGURE

FIG. 1. X-ray structure of Compound 3

INSTRUMENTS

The single crystal was mounted in a capillary. Diffraction was performed on a Bruker SMART DUO CCD area detector diffractometer using graphite-monochromatic Mo-Kα radiation (λ=0.71073 Å) operated at 1500 W power (50 kV, 30 mA).

$^1$H (400 MHz) and $^{13}$C (100 MHz) spectra were recorded with a Bruker Avance III UltraShield-Plus™ Digital NMR spectrometer at room temperature in D$_2$O or DMSO-d$_6$ as solvent. Chemical shifts are reported in ppm relative to TMS or signal of deuterated solvent.

SYNTHETIC EXAMPLES AND EXPERIMENTAL DATA

Example 1: Preparation of 2-amino-6-methyl-pyridine-3,4-dicarboxylic acid (Compound 4)

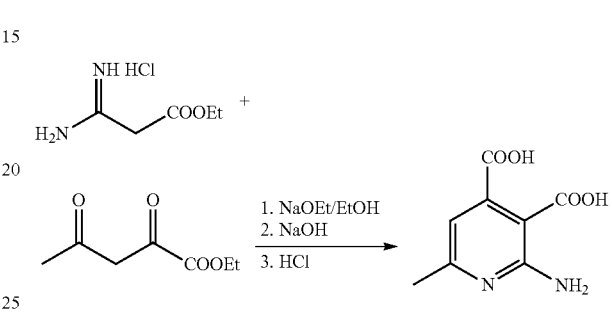

To a solution of 136 mg NaOEt in 2 mL EtOH is added 330 mg of 3-amino-3-imino-propanoic ethyl ester hydrochloride at room temperature. A total of 310 mg of ethyl 2,4-dioxopentanoate is added next. The reaction mixture is heated to reflux for 2 h. Then, 1.6 g of 20% NaOH aq. solution is added under reflux, the mixture is refluxed for another 1 h. It is cooled to room temperature, the reaction mixture is adjusted to pH=5-6. The product is precipitated as solid. It is collected by filtration and washed with 2 mL water twice. A total of 327 mg (yield 85.0%) of the desired product is obtained after being dried at 60° C. in vacuum oven. $^1$H NMR (400 MHz, D$_2$O with NaOD): δ 6.45 (s, 1H), 2.24 (s, 3H); $^{13}$C NMR (100 MHz, D$_2$O with NaOD): δ 177.11, 173.73, 157.99, 156.92, 150.84, 111.45, 111.12, 22.66; MS (m/z+1): 197.1.

Diester 3 is obtained during the above described procedure although not isolated but directly converted into diacid 4. Alternatively, compound 3 is obtained and isolated via the following procedure:

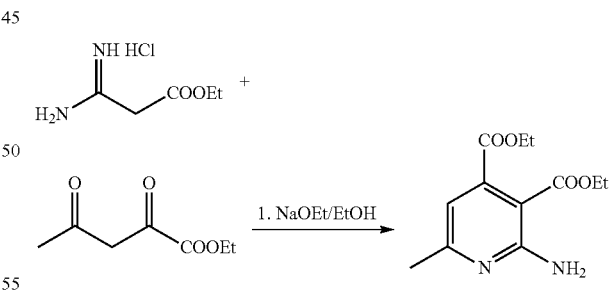

To a solution of 0.29 g of NaOEt in 4.0 mL of EtOH is added 0.7 g of 3-amino-3-imino-propanoic ethyl ester hydrochloride at room temperature, followed by addition of 0.66 g of 2,4-dioxo-pentanoic acid ethyl ester. The reaction mixture is heated to reflux for 2 h. Ethanol is removed by evaporator at 50° C., and then 10 mL of water and 10 mL of ethyl acetate are added and stirred for 10 min. The aqueous phase is then discarded and the organic phase is washed with 10 mL of water. A total of 0.95 g (yield 90.2%) of the desired product (Compound 3) is obtained after the organic phase being concentrated to dryness. $^1$H NMR (400 MHz, D$_2$O with NaOD): δ 6.49 (s, 1H), 6.38 (br, 2H), 4.33 (q, 2H, J=7.2 Hz), 4.29 (q, 2H, J=7.2 Hz), 2.40 (s, 3H), 1.37 (t, 3H, J=7.2 Hz), 1.33 (t, 3H, J=7.2 Hz); $^{13}$C NMR (100 MHz, D$_2$O with NaOD): δ 168.38, 166.26, 163.05, 158.08, 145.27, 111.23, 100.42, 61.74, 61.34, 24.54, 14.09, 13.99; MS (m/z+1): 253.37.

TABLE 1

Crystal data and structure refinement for cd213567 (Compound 3)

| | |
|---|---|
| Identification code | cd213567 |
| Empirical formula | C$_{12}$H$_{16}$N$_2$O$_4$ |
| Formula weight | 252.27 |
| Temperature | 293(2) K |
| Wavelength | 0.71073 Å |
| Crystal system, space group | Monoclinic, P2(1)/c |
| Unit cell dimensions | a = 8.4904 (9) Å alpha = 90 deg. |
| | b = 10.7915 (10) Å beta = 91.236(2) deg. |
| | c = 14.6320 (15) Å gamma = 90 deg. |
| Volume | 1340.3 (2) Å$^3$ |
| Z, calculated density | 4, 1.250 mg/m$^3$ |
| Absorption coefficient | 0.095 mm$^{-1}$ |
| F(000) | 536 |
| Crystal size | 0.21 × 0.15 × 0.11 mm |
| Theta range for data collection | 2.35 to 26.00 deg |
| Limiting indices | –0 <= h <= 10, –11 <= K <= 13, –18 <= l <= 17 |
| Reflections collected/unique | 7961/2627 [R(int) = 0.0355] |
| Completeness to theta = 26.00 | 100.0% |
| Absorption correction | Empirical |
| Max. and min. transmission | 1.00000 and 0.59772 |
| Refinement method | Full-matrix least-squares on F$^2$ |
| Data/restraints/parameters | 2627/50/194 |
| Goodness-of-fit on F$^2$ | 1.059 |
| Final R indices [I > 2sigma(I)] | R1 = 0.0589, wR2 = 0.1738 |
| R indices (all data) | R1 = 0.0794, wR2 = 0.1926 |
| Extinction coefficient | 0.008(4) |
| Largest diff. Peak and hole | 0.234 and –0.185 e.Å$^{-3}$ |

TABLE 2

Atomic coordinates and equivalent isotropic displacement parameters (Å$^2$) for cd213567 (Compound 3).
U(eq) is defined as one third of the trace of the orthogonalized Uij tensor.

| | x | y | z | U (eq) |
|---|---|---|---|---|
| N1 | 0.90561 (19) | 0.56682 (15) | 0.10675 (11) | 0.0590 (5) |
| N2 | 0.9389 (3) | 0.6643 (2) | –0.02969 (13) | 0.0851 (7) |
| O1 | 0.8120 (3) | 0.89046 (19) | –0.04855 (12) | 0.1279 (9) |
| O2 | 0.7365 (2) | 0.98258 (14) | 0.07604 (11) | 0.0819 (6) |
| O3 | 0.4995 (2) | 0.8713 (2) | 0.19328 (13) | 0.1005 (7) |
| O4 | 0.7028 (2) | 0.92509 (18) | 0.28122 (12) | 0.1020 (7) |
| C1 | 0.8796 (2) | 0.66852 (19) | 0.05502 (13) | 0.0599 (5) |
| C2 | 0.7987 (2) | 0.77321 (18) | 0.08814 (12) | 0.0565 (5) |
| C3 | 0.7413 (2) | 0.76564 (18) | 0.17680 (12) | 0.0541 (5) |
| C4 | 0.7716 (2) | 0.66224 (18) | 0.22928 (13) | 0.0585 (5) |
| C5 | 0.8548 (2) | 0.56481 (18) | 0.19211 (13) | 0.0568 (5) |
| C6 | 0.8883 (3) | 0.4505 (2) | 0.24673 (16) | 0.0785 (7) |
| C7 | 0.7828 (3) | 0.8846 (2) | 0.03107 (15) | 0.0715 (6) |
| C8 | 0.7145 (4) | 1.0975 (2) | 0.0244 (2) | 0.1038 (10) |
| C9 | 0.6481 (7) | 1.1880 (3) | 0.0857 (3) | 0.171 (2) |
| C10 | 0.6339 (3) | 0.8605 (2) | 0.21610 (14) | 0.0678 (6) |
| C11 | 0.6404 (11) | 1.0437 (8) | 0.3202 (6) | 0.1134 (18) |
| C12 | 0.5778 (11) | 1.0088 (9) | 0.4047 (5) | 0.135 (2) |
| C11' | 0.5747 (9) | 1.0007 (7) | 0.3256 (6) | 0.1062 (17) |
| C12' | 0.6772 (9) | 1.0941 (7) | 0.3767 (6) | 0.121 (2) |

TABLE 3

Bond lengths [Å] and angles [deg] for cd213567 (Compound 3).

| | |
|---|---|
| N1—C5 | 1.330(2) |
| N1—C1 | 1.349(3) |

TABLE 3-continued

Bond lengths [Å] and angles [deg] for cd213567 (Compound 3).

| | |
|---|---|
| N2—C1 | 1.349(3) |
| N2—H2A | 0.95(3) |
| N2—H2B | 0.91(3) |
| O1—C7 | 1.198(3) |
| O2—C7 | 1.310(3) |
| O2—C8 | 1.462(3) |
| O3—C10 | 1.188(3) |
| O4—C10 | 1.308(3) |
| O4—C11 | 1.503(8) |
| O4—C11' | 1.516(7) |
| C1—C2 | 1.413(3) |
| C2—C3 | 1.398(3) |
| C2—C7 | 1.469(3) |
| C3—C4 | 1.376(3) |
| C3—C10 | 1.494(3) |
| C4—C5 | 1.384(3) |
| C4—H4 | 0.93 |
| C5—C6 | 1.494(3) |
| C6—H6A | 0.96 |
| C6—H6B | 0.96 |
| C6—H6C | 0.96 |
| C8—C9 | 1.449(4) |
| C8—H8A | 0.97 |
| C8—H8B | 0.97 |
| C9—H9A | 0.96 |
| C9—H9B | 0.96 |
| C9—H9C | 0.96 |
| C11—C12 | 1.408(11) |
| C11—H11A | 0.97 |
| C11—H11B | 0.97 |
| C12—H12A | 0.96 |
| C12—H12B | 0.96 |
| C12—H12C | 0.96 |
| C11'—C12' | 1.518(9) |
| C11'—H11C | 0.97 |
| C11'—H11D | 0.97 |
| C12'—H12D | 0.96 |
| C12'—H12E | 0.96 |
| C12'—H12F | 0.96 |
| C5—N1—C1 | 119.18(16) |
| C1—N2—H2A | 117.1(15) |
| C1—N2—H2B | 117.2(16) |
| H2A—N2—H2B | 124(2) |
| C7—O2—C8 | 117.44(18) |
| C10—O4—C11 | 125.1(4) |
| C10—O4—C11' | 106.6(3) |
| C11—O4—C11' | 28.0(4) |
| N2—C1—N1 | 115.36(18) |
| N2—C1—C2 | 122.42(19) |
| N1—C1—C2 | 122.21(17) |
| C3—C2—C1 | 116.96(18) |
| C3—C2—C7 | 123.09(18) |
| C1—C2—C7 | 119.92(18) |
| C4—C3—C2 | 120.02(17) |
| C4—C3—C10 | 116.71(17) |
| C2—C3—C10 | 123.03(18) |
| C3—C4—C5 | 119.19(18) |
| C3—C4—H4 | 120.4 |
| C5—C4—H4 | 120.4 |
| N1—C5—C4 | 122.35(18) |
| N1—C5—C6 | 116.98(18) |
| C4—C5—C6 | 120.66(18) |
| C5—C6—H6A | 109.5 |
| C5—C6—H6B | 109.5 |
| H6A—C6—H6B | 109.5 |
| C5—C6—H6C | 109.5 |
| H6A—C6—H6C | 109.5 |
| H6B—C6—H6C | 109.5 |
| O1—C7—O2 | 121.1(2) |
| O1—C7—C2 | 125.3(2) |
| O2—C7—C2 | 113.57(18) |
| C9—C8—O2 | 107.4(2) |
| C9—C8—H8A | 110.2 |
| O2—C8—H8A | 110.2 |
| C9—C8—H8B | 110.2 |
| O2—C8—H8B | 110.2 |
| H8A—C8—H8B | 108.5 |
| C8—C9—H9A | 109.5 |

TABLE 3-continued

Bond lengths [Å] and angles [deg] for cd213567 (Compound 3).

| | |
|---|---|
| C8—C9—H9B | 109.5 |
| H9A—C9—H9B | 109.5 |
| C8—C9—H9C | 109.5 |
| H9A—C9—H9C | 109.5 |
| H9B—C9—H9C | 109.5 |
| O3—C10—O4 | 124.3(2) |
| O3—C10—C3 | 123.4(2) |
| O4—C10—C3 | 112.23(18) |
| C12—C11—O4 | 104.4(7) |
| C12—C11—H11A | 110.9 |
| O4—C11—H11A | 110.9 |
| C12—C11—H11B | 110.9 |
| O4—C11—H11B | 110.9 |
| H11A—C11—H11B | 108.9 |
| O4—C11'—C12' | 99.2(5) |
| O4—C11'—H11C | 111.9 |
| C12'—C11'—H11C | 111.9 |
| O4—C11'—H11D | 111.9 |
| C12'—C11'—H11D | 111.9 |
| H11C—C11'—H11D | 109.6 |
| C11'—C12'—H12D | 109.5 |
| C11'—C12'—H12E | 109.5 |
| H12D—C12'—H12E | 109.5 |
| C11'—C12'—H12F | 109.5 |
| H12D—C12'—H12F | 109.5 |
| H12E—C12'—H12F | 109.5 |

Symmetry Transformations Used to Generate Equivalent Atoms:

TABLE 4

Anisotropic displacement parameters (Å$^2$) for cd213567 (Compound 3).
The anisotropic displacement factor exponent takes the form:
−2 pi^2 [h^2 a*^2 U11 + . . . + 2 h k a* b* U12 ]

| | U11 | U22 | U33 | U12 | U13 | U23 |
|---|---|---|---|---|---|---|
| N1 | 0.0666 (10) | 0.0616 (10) | 0.0491 (9) | 0.0066 (8) | 0.0108 (7) | −0.0051 (7) |
| N2 | 0.1334 (19) | 0.0725 (13) | 0.0505 (11) | 0.0221 (13) | 0.0304 (11) | −0.0020 (10) |
| O1 | 0.236 (3) | 0.0952 (13) | 0.0538 (11) | 0.0561 (15) | 0.0306 (13) | 0.0107 (9) |
| O2 | 0.1212 (14) | 0.0625 (9) | 0.0626 (10) | 0.0156 (9) | 0.0178 (9) | 0.0001 (7) |
| O3 | 0.0676 (11) | 0.1343 (16) | 0.1000 (14) | 0.0346 (10) | 0.0083 (9) | −0.0016 (12) |
| O4 | 0.1105 (14) | 0.1155 (14) | 0.0795 (11) | 0.0534 (11) | −0.0094 (10) | −0.0456 (10) |
| C1 | 0.0702 (12) | 0.0672 (12) | 0.0426 (10) | 0.0044 (10) | 0.0088 (9) | −0.0074 (9) |
| C2 | 0.0643 (12) | 0.0630 (12) | 0.0422 (10) | 0.0068 (9) | 0.0030 (8) | −0.0061 (8) |
| C3 | 0.0501 (10) | 0.0675 (12) | 0.0447 (10) | 0.0051 (8) | 0.0012 (7) | −0.0084 (9) |
| C4 | 0.0605 (11) | 0.0725 (12) | 0.0430 (10) | 0.0059 (9) | 0.0107 (8) | −0.0018 (9) |
| C5 | 0.0567 (11) | 0.0654 (12) | 0.0485 (10) | 0.0015 (9) | 0.0069 (8) | −0.0029 (9) |
| C6 | 0.0932 (17) | 0.0784 (14) | 0.0648 (13) | 0.0186 (12) | 0.0195 (12) | 0.0106 (11) |
| C7 | 0.0934 (16) | 0.0733 (14) | 0.0481 (12) | 0.0150 (12) | 0.0060 (10) | −0.0052 (10) |
| C8 | 0.151 (3) | 0.0728 (16) | 0.088 (2) | 0.0191 (16) | 0.0219 (18) | 0.0138 (14) |
| C9 | 0.299 (6) | 0.080 (2) | 0.137 (3) | 0.054 (3) | 0.071 (4) | 0.016 (2) |
| C10 | 0.0708 (14) | 0.0831 (14) | 0.0499 (12) | 0.0205 (11) | 0.0106 (10) | 0.0014 (10) |
| C11 | 0.125 (4) | 0.123 (4) | 0.093 (3) | 0.048 (3) | 0.003 (3) | −0.045 (3) |
| C12 | 0.153 (5) | 0.145 (5) | 0.107 (4) | 0.049 (4) | 0.019 (4) | −0.030 (4) |
| C11' | 0.119 (4) | 0.112 (3) | 0.087 (3) | 0.043 (3) | 0.010 (3) | −0.048 (3) |
| C12' | 0.132 (4) | 0.114 (4) | 0.116 (4) | 0.042 (3) | −0.004 (4) | −0.059 (4) |

TABLE 5

Hydrogen coordinates and isotropic displacement parameters (Å$^2$) for cd213567 (Compound 3).

| | x | y | z | U(eq) |
|---|---|---|---|---|
| H4 | 0.7367 | 0.6578 | 0.289 | 0.070 |
| H6A | 0.9008 | 0.3814 | 0.2062 | 0.118 |
| H6B | 0.8024 | 0.4347 | 0.2867 | 0.118 |
| H6C | 0.9834 | 0.4619 | 0.2824 | 0.118 |
| H8A | 0.8147 | 1.1266 | 0.002 | 0.125 |
| H8B | 0.6438 | 1.0837 | −0.0276 | 0.125 |
| H9A | 0.5501 | 1.1576 | 0.1082 | 0.257 |
| H9B | 0.6302 | 1.2643 | 0.0534 | 0.257 |

TABLE 5-continued

Hydrogen coordinates and isotropic displacement parameters (Å$^2$) for cd213567 (Compound 3).

| | x | y | z | U(eq) |
|---|---|---|---|---|
| H9C | 0.7201 | 1.2022 | 0.1361 | 0.257 |
| H11A | 0.7241 | 1.104 | 0.3287 | 0.136 |
| H11B | 0.5592 | 1.0788 | 0.2803 | 0.136 |
| H12A | 0.4855 | 0.9589 | 0.3944 | 0.202 |
| H12B | 0.5502 | 1.0817 | 0.4385 | 0.202 |
| H12C | 0.655 | 0.9621 | 0.439 | 0.202 |
| H11C | 0.5126 | 0.9511 | 0.3667 | 0.127 |
| H11D | 0.5058 | 1.0402 | 0.2806 | 0.127 |
| H12D | 0.7422 | 1.0518 | 0.4211 | 0.181 |
| H12E | 0.6113 | 1.1529 | 0.407 | 0.181 |
| H12F | 0.7427 | 1.1367 | 0.3342 | 0.181 |
| H2A | 0.978 (3) | 0.586 (2) | −0.0501 (17) | 0.079 (7) |
| H2B | 0.916 (3) | 0.729 (3) | −0.0680 (17) | 0.084 (8) |

TABLE 6

Torsion angles [deg] for cd213567 (Compound 3).

| | |
|---|---|
| C5—N1—C1—N2 | 178.17(19) |
| C5—N1—C1—C2 | −0.5(3) |
| N2—C1—C2—C3 | 179.3(2) |
| N1—C1—C2—C3 | −2.1(3) |
| N2—C1—C2—C7 | −2.7(3) |

TABLE 6-continued

Torsion angles [deg] for cd213567 (Compound 3).

| | |
|---|---|
| N1—C1—C2—C7 | 175.92(19) |
| C1—C2—C3—C4 | 3.4(3) |
| C7—C2—C3—C4 | −174.57(19) |
| C1—C2—C3—C10 | −170.79(19) |
| C7—C2—C3—C10 | 11.3(3) |
| C2—C3—C4—C5 | −2.1(3) |
| C10—C3—C4—C5 | 172.39(18) |
| C1—N1—C5—C4 | 1.9(3) |
| C1—N1—C5—C6 | −179.32(19) |
| C3—C4—C5—N1 | −0.6(3) |
| C3—C4—C5—C6 | −179.31(19) |

TABLE 6-continued

Torsion angels [deg] for cd213567 (Compound 3).

| | |
|---|---|
| C8—O2—C7—O1 | 2.9(4) |
| C8—O2—C7—C2 | −178.9(2) |
| C3—C2—C7—O1 | −170.0(3) |
| C1—C2—C7—O1 | 12.1(4) |
| C3—C2—C7—O2 | 11.8(3) |
| C1—C2—C7—O2 | −166.12(19) |
| C7—O2—C8—C9 | 174.1(3) |
| C11—O4—C10—O3 | −17.2(6) |
| C11'—O4—C10—O3 | 6.4(5) |
| C11—O4—C10—C3 | 166.1(5) |
| C11'—O4—C10—C3 | −170.3(4) |
| C4—C3—C10—O3 | −102.2(3) |
| C2—C3—C10—O3 | 72.2(3) |
| C4—C3—C10—O4 | 74.6(3) |
| C2—C3—C10—O4 | −111.1(2) |
| C10—O4—C11—C12 | 103.4(8) |
| C11'—O4—C11—C12 | 48.7(11) |
| C10—O4—C11'—C12' | −164.0(6) |
| C11—O4—C11'—C12' | −28.2(10) |

Symmetry Transformations Used to Generate Equivalent Atoms:

TABLE 7

Hydrogen bonds for cd213567 (Compound 3) [Å and deg.].

| D—H . . . A | D(D—H) | D(H . . . A) | D(D . . . A) | <(DHA) |
|---|---|---|---|---|
| N2—H2B . . . O1 | 0.91(3) | 1.98(3) | 2.680(3) | 133(2) |
| N2—H2A . . . N(1)#1 | 0.95(3) | 2.11(3) | 3.049(3) | 170(2) |

1−x + 2, −y + 1, −z

Symmetry Transformations Used to Generate Equivalent Atoms:

Example 2: Preparation of 2-amino-6-methyl-isonicotinic acid (Compound 5)

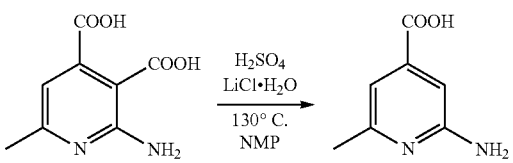

To a slurry of 154 mg of 2-amino-6-methyl-pyridine-3,4-dicarboxylic acid in 0.65 mL of NMP are added 50 mg of LiCl.H$_2$O and 190 mg of conc. H$_2$SO$_4$. The reaction mixture is heated to 130° C. and stirred for 48 h. It is then cooled to 20-30° C., and 1.6 mL of water is added. The resulting reaction mixture is adjusted to pH=6-7. The product is precipitated as solid. It is collected by filtration and washed with 1 mL water twice. A total of 100 mg (yield 83.7%) of the desired product is obtained after being dried at 60° C. in vacuum oven. $^1$H NMR (400 MHz, D$_2$O with NaOD): δ 6.69 (s, 1H), 6.61 (s, 1H), 2.13 (s, 3H); $^{13}$C NMR: (100 MHz, D$_2$O with NaOD) δ 177.78, 158.62, 156.05, 147.21, 112.60, 106.08, 22.66; MS (m/z+1): 153.1.

Example 3: Preparation of 2-amino-6-methyl-isonicotinic acid methyl ester (Compound 6)

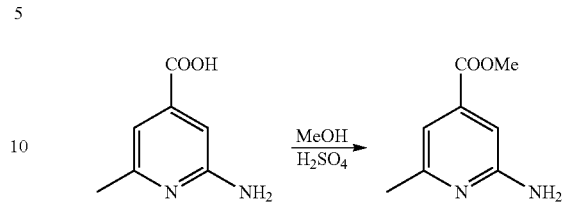

To a slurry of 340 mg of 2-amino-6-methyl-isonicotinic acid in 1.6 mL of methanol is added 170 mg of conc. sulfuric acid slowly at room temperature. The reaction mixture is heated to reflux for 6 h and then cooled to room temperature. Methanol is removed by evaporator at 50° C. A total of 1.6 mL of water is added and the mixture is adjusted to pH=6.5-7.0. The product is precipitated as solid. It is collected by filtration and washed with 1 mL water twice. A total of 190 mg (yield 51.2%) of the desired product is obtained after being dried at 60° C. in vacuum oven. $^1$H NMR (400 MHz, DMSO-d$_6$): δ 6.78 (d, 2H), 6.24 (s, 2H), 3.84 (s, 3H), 2.31 (s, 3H); $^{13}$C NMR (100 MHz, DMSO-d$_6$): δ 165.06, 160.00, 157.32, 138.21, 109.33, 104.49, 52.20, 23.74; MS (m/z+1): 167.1.

Example 4: Preparation of 2-amino-6,N,N-trimethyl-isonicotinamide (Compound 7)

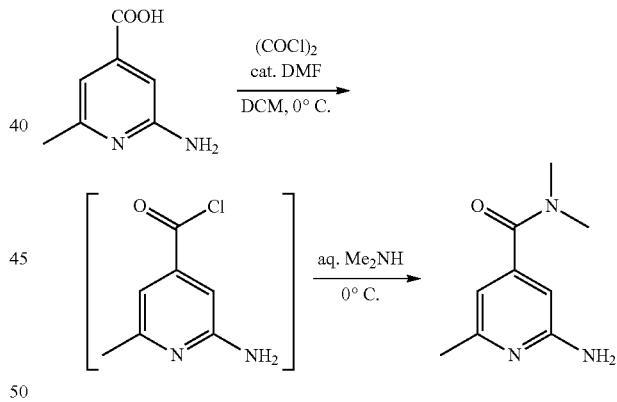

To a slurry of 110 mg of 2-amino-6-methyl-isonicotinic acid in 1.1 mL of dichloromethane is added 0.01 mL of DMF. The mixture is cooled to 0-5° C. and 122 mg of oxalyl chloride is added slowly. The reaction mixture is stirred at 0-5° C. for 1 h, and then 400 mg of 40% dimethylamine aq. solution is added dropwise. The mixture is stirred for 1 h, followed by addition of 50 mg of NaCl. The organic phase is separated. The aqueous phase is extracted by 0.4 mL dichloromethane twice. The combined organic phase is washed with 0.3 mL of 25% sodium chloride aq. solution. It is then concentrated by evaporator and 1 mL of toluene is added. The resulting solid is collected by filtration and washed with 1 mL of toluene. A total of 94 mg (yield 72.0%) of the desired product is obtained after being dried at 60° C. in vacuum oven. $^1$H NMR (400 MHz, DMSO-d$_6$): δ 6.28 (s, 1H), 6.14 (s, 1H), 6.06 (s, 2H), 2.93 (s, 3H), 2.86 (s, 3H), 2.24 (s, 3H); ¹³C NMR (100 MHz, DMSO-d₆): δ 168.97, 159.31, 156.45, 145.57, 107.95, 101.95, 34.18, 32.76; MS (m/z+1): 180.2.

Example 5: Preparation of 2-amino-6-ethyl-pyridine-3,4-dicarboxylic acid (Compound 10a)

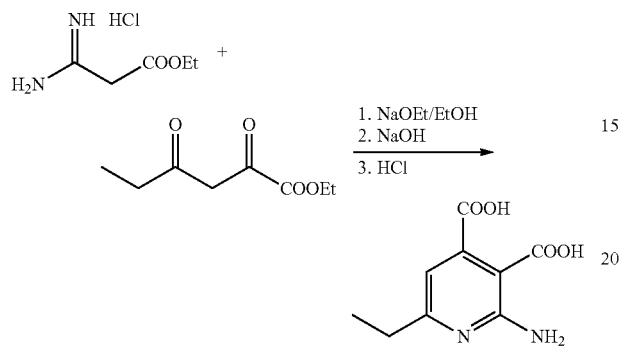

To a solution of 136 mg of NaOEt in 2 mL of EtOH is added 330 mg of 3-amino-3-imino-propanoic ethyl ester hydrochloride at room temperature, followed by addition of 340 mg of ethyl 2,4-dioxohexanoate. The reaction mixture is heated to reflux for 2 h. A total of 1.6 g of 20% NaOH aq. solution is added under reflux. The mixture was refluxed for another 1 h then cooled to room temperature. It is adjusted to pH=5-6. The product is precipitated as solid. It is collected by filtration and washed with 2 mL of water twice. A total of 350 mg (yield 84.3%) of the desired product is obtained after being dried at 60° C. in vacuum oven. ¹H NMR (400 MHz, D₂O with NaOD): δ 6.45 (s, 1H), 2.47 (q, 2H), 2.08 (t, 3H); ¹³C NMR (100 MHz, D₂O with NaOD): δ 177.17, 173.79, 163.34, 156.94, 150.92, 111.74, 109.81, 29.99, 13.16; MS (m/z+1): 211.1.

Example 6: Preparation of 2-amino-6-ethyl-isonicotinic acid (Compound 11a)

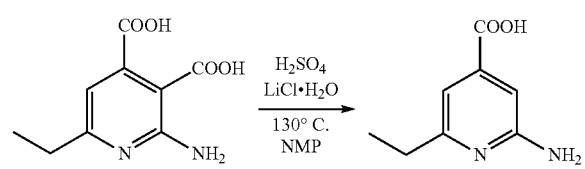

To a slurry of 165 mg of 2-amino-6-ethyl-pyridine-3,4-dicarboxylic acid in 0.65 mL of NMP are added 50 mg of LiCl.H₂O and 190 mg of conc. H₂SO₄. The reaction mixture is heated to 130° C. for 48 h, then cooled to 20-30° C. A total of 1.6 mL of water is added. The reaction mixture is adjusted to pH=6-7. The product is precipitated as solid. It is collected by filtration and washed with 1 mL of water twice. A total of 110 mg (yield 84.3%) of the desired product is obtained after being dried at 60° C. in vacuum oven. ¹H NMR (400 MHz, D₂O with NaOD): δ 6.79 (s, 1H), 6.14 (s, 1H), 2.47 (q, 2H), 1.05 (t, 3H); ¹³C NMR (100 MHz, D₂O with NaOD): δ 173.99, 162.53, 158.84, 147.61, 111.26, 106.30, 30.00, 13.35; MS (m/z+1): 167.1.

Example 7: Preparation of 2-amino-6-isopropyl-pyridine-3,4-dicarboxylic acid (Compound 10b)

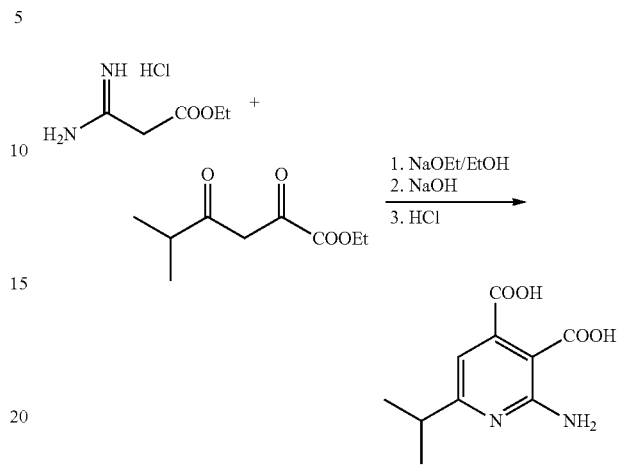

To a solution of 74 mg of NaOEt in 1 mL of EtOH, is added 180 mg of 3-amino-3-imino-propanoic ethyl ester hydrochloride at room temperature, followed by addition of 200 mg of ethyl 5-methyl-2,4-dioxohexanoate. The reaction mixture is heated to reflux for 2 h. A total of 860 mg of 20% NaOH aq. solution is added under reflux. The reaction mixture is refluxed for another 1 h, and then cooled to room temperature. It is adjusted to pH=5-6. The crude product is obtained by removing solvent completely, which is used to the next step directly. ¹H NMR (400 MHz, D₂O with NaOD): δ 6.63 (s, 1H), 2.88 (m, 1H), 1.25 (d, 6H); ¹³C NMR (100 MHz, D₂O with NaOD): δ 177.25, 173.83, 167.35, 156.79, 150.86, 111.87, 108.04, 35.25, 21.52; MS (m/z+1): 225.1.

Example 8: Preparation of 2-amino-6-isopropyl-isonicotinic acid (Compound 11b)

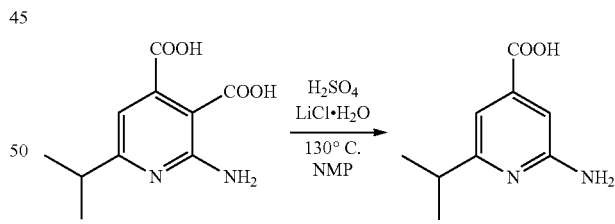

To a slurry of the above 2-amino-6-isopropyl-pyridine-3,4-dicarboxylic acid in 1 mL of NMP are added 65 mg of LiCl.H₂O and 265 mg of conc. H₂SO₄. The reaction mixture is heated to 130° C. for 48 h, and then cooled to 20-30° C. A total of 2.5 mL of water is added. The mixture is adjusted to pH=6-7. The product is precipitated as solid. It is collected by filtration and washed with 1 mL of water twice. A total of 135 mg (yield 69.7% in 2 steps) of the desired product is obtained after being dried at 60° C. in vacuum oven. ¹H NMR (400 MHz, D₂O with NaOD): δ 7.00 (s, 1H), 6.86 (s, 1H), 2.88 (m, 1H), 1.25 (d, 6H); ¹³C NMR (100 MHz, D₂O with NaOD): δ 173.99, 166.71, 158.06, 147.77, 109.59, 106.56, 35.30, 21.75; MS (m/z+1): 181.0.

Example 9: Preparation of 2-amino-6-tert-butyl-pyridine-3,4-dicarboxylic acid (Compound 10c)

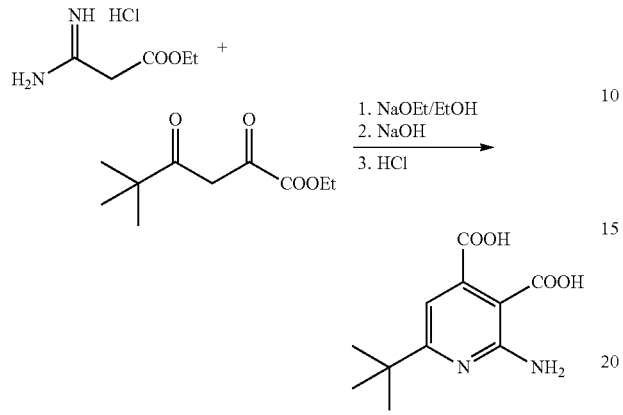

To a solution of 68 mg of NaOEt in 1 mL of EtOH is added 166 mg of 3-amino-3-imino-propanoic ethyl ester hydrochloride at room temperature, followed by addition of 200 mg of ethyl 5,5-dimethyl-2,4-dioxohexanoate. The reaction mixture is heated to reflux for 2 h. A total of 790 mg of 20% NaOH aq. solution is added under reflux. The mixture is refluxed for another 1 h, and then cooled to room temperature. It is adjusted to pH=5-6. The crude product is obtained by removing solvent completely, which is used to the next step directly. $^1$H NMR (400 MHz, D$_2$O with NaOD): δ 6.57 (s, 1H), 1.10 (s, 9H); $^{13}$C NMR (100 MHz, D$_2$O with NaOD): δ 177.24, 173.96, 169.12, 156.66, 150.26, 111.80, 107.42, 36.25, 29.06; MS (m/z+1): 239.0.

Example 10: Preparation of 2-amino-6-tert-butyl-isonicotinic acid (Compound 11c)

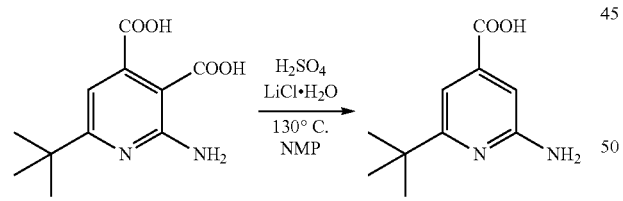

To a slurry of above 2-amino-6-tert-butyl-pyridine-3,4-dicarboxylic acid in 1 mL of NMP are added 65 mg of LiCl.H$_2$O and 245 mg of conc. H$_2$SO$_4$. The reaction mixture is heated to 140° C. for 48 h, and then cooled to 20-30° C. A total of 2.5 mL of water is added. The mixture is adjusted to pH=6-7. The product is precipitated as solid. It is collected by filtration and washed with 1 mL of water twice. A total of 115 mg (yield 59.3% in 2 steps) of the desired product is obtained after being dried at 60° C. in vacuum oven. $^1$H NMR (400 MHz, D$_2$O with NaOD): δ 6.93 (s, 1H), 6.62 (s, 1H), 1.10 (s, 9H); $^{13}$C NMR (100 MHz, D$_2$O with NaOD): δ 174.13, 168.73, 158.95, 147.32, 108.85, 106.40, 36.35, 29.32; MS (m/z+1): 195.1.

Example 11: Preparation of 2-amino-6-phenyl-pyridine-3,4-dicarboxylic acid (Compound 10d)

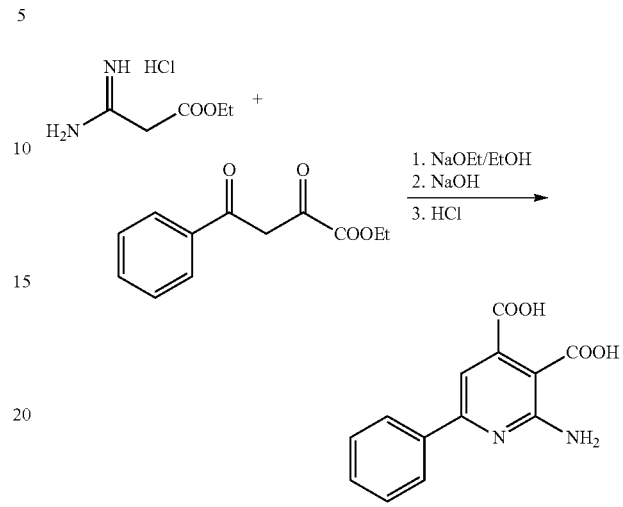

To a solution of 136 mg of NaOEt in 2 mL of EtOH is added 330 mg of 3-amino-3-imino-propanoic ethyl ester hydrochloride at room temperature, followed by addition of 440 mg of 2,4-dioxo-4-phenyl-butyric acid ethyl ester. The reaction mixture is heated to reflux for 2 h. A total of 1600 mg of 20% NaOH aq. solution is added under reflux. The mixture is refluxed for another 1 h, and then cooled to room temperature. It is adjusted to pH=5-6. The product is precipitated as solid. It is collected by filtration, and washed with 1 mL of water twice. A total of 405 mg (yield 78.5%) of the desired product is obtained after being dried in vacuum oven at 60° C. $^1$H NMR (400 MHz, D$_2$O with NaOD): δ 6.67 (q, 2H), 7.35 (q, 3H), 6.90 (s, 1H); $^{13}$C NMR (100 MHz, D$_2$O with NaOD): δ 176.74, 173.71, 157.35, 156.43, 150.68, 138.23, 129.41, 128.03, 127.03, 113.11, 109.34; MS (m/z+1): 259.1.

Example 12: Preparation of 2-amino-6-phenyl-isonicotinic acid (Compound 11d)

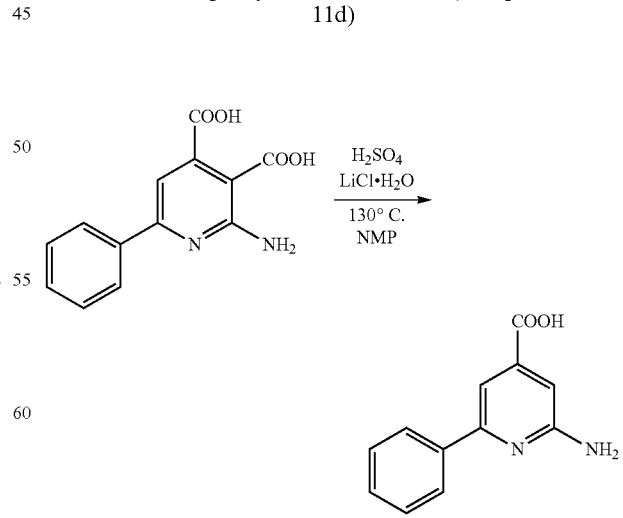

To a slurry of 258 mg of 2-amino-6-phenyl-pyridine-3,4-dicarboxylic acid in 1 mL of NMP is added 60 mg of LiCl.H$_2$O and 245 mg of conc. H$_2$SO$_4$. The reaction mixture is heated to 130° C. for 48 h and then cooled to 20-30° C. A total of 2.5 mL of water is added. The mixture is adjusted to pH=6-7. The product is precipitated as solid. It is collected by filtration and washed with 1 mL of water twice. A total of 180 mg (yield 84.1%) of the desired product is obtained after being dried at 60° C. in vacuum oven. $^1$H NMR (400 MHz, D$_2$O with NaOD): δ 7.49 (q, 2H), 7.23 (q, 3H), 7.13 (s, 1H), 6.75 (s, 1H); $^{13}$C NMR (100 MHz, D$_2$O with NaOD): δ 173.53, 159.47, 156.17, 147.69, 138.69, 129.07, 128.77, 126.96, 111.13, 107.67; MS (m/z+1): 215.0.

Example 13: Preparation of 2-amino-6-ethyl-5-methyl-pyridine-3,4-dicarboxylic acid (Compound 14a)

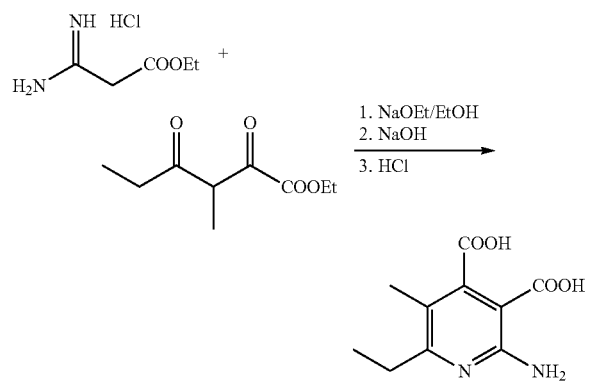

To a solution of 74 mg of NaOEt in 1 mL of EtOH is added 180 mg of 3-amino-3-imino-propanoic ethyl ester hydrochloride at room temperature, followed by addition of 200 mg of ethyl 3-methyl-2,4-dioxohexanoate. The reaction mixture is heated to reflux for 2 h. A total of 1.29 g of 20% NaOH aq. solution is added under reflux. The mixture is reflux for another 3 h, and then cooled to room temperature. It is adjusted to pH=5-6. The crude product is obtained by removing solvent completely, which was used to the next step directly. $^1$H NMR (400 MHz, D$_2$O with NaOD): δ 2.68 (q, 2H), 2.14 (s, 3H), 1.18 (t, 3H); $^{13}$C NMR (100 MHz, D$_2$O with NaOD): δ 177.40, 173.61, 162.06, 155.43, 151.94, 115.49, 110.70, 28.06, 13.72, 12.67; MS (m/z+1): 225.1.

Example 14: Preparation of 2-amino-6-ethyl-5-methyl-isonicotinic acid (Compound 15a)

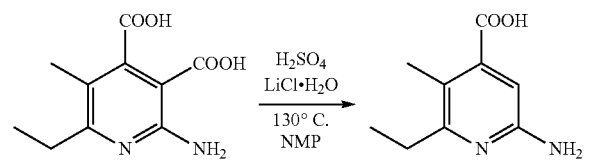 [SMILES: CCc1nc(N)c(C(=O)O)c(C(=O)O)c1C ; CCc1nc(N)cc(C(=O)O)c1C]

To a slurry of above 2-amino-6-ethyl-5-methyl-pyridine-3,4-dicarboxylic acid in 1 mL of NMP are added 65 mg of LiCl.H$_2$O and 265 mg of conc. H$_2$SO$_4$. The reaction mixture is heated to 130° C. for 48 h, and then cooled to 20-30° C. A total of 2.5 mL of water is added. The mixture is adjusted to pH=6-7. The product is precipitated as solid. It is collected by filtration and washed with 1 mL of water twice. A total of 118 mg (yield 61.0% in 2 steps) of the desired product is obtained after being dried at 60° C. in vacuum oven. $^1$H NMR (400 MHz, D$_2$O with NaOD): δ 6.21 (s, 1H), 2.43 (q, 2H), 1.95 (s, 3H), 0.94 (t, 3H); $^{13}$C NMR (100 MHz, D$_2$O with NaOD): δ 177.17, 160.40, 156.04, 151.58, 115.57, 103.37, 27.71, 13.47, 12.69; MS (m/z+1): 181.1.

Example 15: Preparation of 2-amino-6,7-dihydro-5H-cyclopenta[b]pyridine-3,4-dicarboxylic acid (Compound 14b)

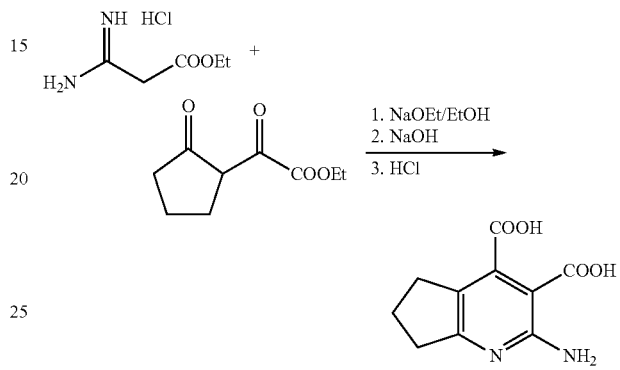

To a solution of 74 mg of NaOEt in 1 mL of EtOH is added 180 mg of 3-amino-3-imino-propanoic ethyl ester hydrochloride at room temperature, followed by addition of 200 mg of 2-oxo-cyclopentanecarboxylic acid ethyl ester. The reaction mixture is heated to reflux for 2 h. A total of 860 mg of 20% NaOH aq. solution is added under reflux. The mixture is refluxed for another 1 h, and then cooled to room temperature. It is adjusted to pH=5-6. The product is precipitated as solid. It is collected by filtration and washed with 1 mL of water twice. A total of 200 mg (yield 82.9%) of the desired product is obtained after being dried at 60° C. in vacuum oven. $^1$H NMR (400 MHz, D$_2$O with NaOD): δ 2.68 (t, 2H), 2.61 (t, 2H), 1.95 (m, 2H); $^{13}$C NMR (100 MHz, D$_2$O with NaOD): δ 176.77, 173.75, 165.36, 157.06, 147.52, 122.96, 110.19, 33.51, 28.31, 22.42; MS (m/z+1): 223.1.

Example 16: Preparation of 2-amino-6,7-dihydro-5H-cyclopenta[b]pyridine-4-carboxylic acid (Compound 15b)

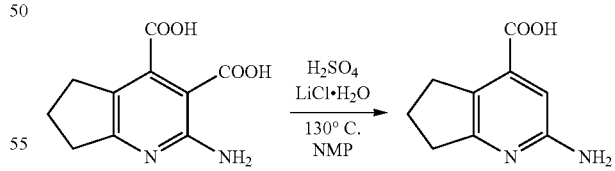

To a slurry of 200 mg of 2-amino-6,7-dihydro-5H-cyclopenta[b]pyridine-3,4-dicarboxylic acid in 0.8 mL of NMP are added 54 mg of LiCl.H$_2$O and 216 mg of conc. H$_2$SO$_4$. The reaction mixture is heated to 130° C. for 48 h, and then cooled to 20-30° C. A total of 2 mL of water is added. The mixture is adjusted to pH=6-7. The product is precipitated as solid. It is collected by filtration and washed with 1 mL of water twice. A total of 120 mg (yield 74.8%) of the desired product is obtained after being dried at 60° C. in vacuum oven. $^1$H NMR (400 MHz, D$_2$O with NaOD): δ 6.37 (s, 1H), 2.64 (t, 2H), 2.50 (t, 2H), 1.76 (m, 2H); $^{13}$CNMR (100 MHz, D$_2$O with NaOD): δ 175.13, 164.23, 157.65, 144.80, 125.10, 104.95, 33.08, 29.26, 22.25; MS (m/z+1): 179.0.

The invention claimed is:

1. A process for preparing 2-amino-isonicotinic acid derivatives of formula I

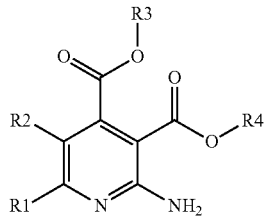

in which
R1 is C$_1$-C$_6$-alkyl- or C$_6$-C$_{10}$-aryl-;
R2 is H—, C$_1$-C$_6$-alkyl- or C$_6$-C$_{10}$-aryl-;
or
R1 and R2 together form a C$_2$-C$_5$-alkyl-group such that a ring is formed;
R3 is C$_1$-C$_4$-alkyl-;
R4 is C$_1$-C$_4$-alkyl-;
comprising the reaction of compound (1)

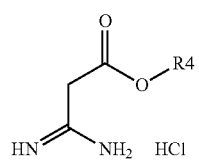

with a compound of formula II

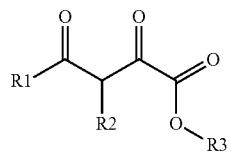

in which R1, R2, R3 and R4 have the meaning as in formula I,
in which water is eliminated.

2. The process according to claim 1, further comprising hydrolyzing the ester groups —COOR3 and —COOR4 of the 2-amino-isonicotinic acid derivatives of formula I to give intermediate compound of formula III

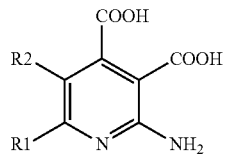

in which R1 and R2 have the meaning as in formula I.

3. The process according to claim 2, further comprising reacting the intermediate compound of formula III under conditions facilitating decarboxylation to give a compound of formula IV

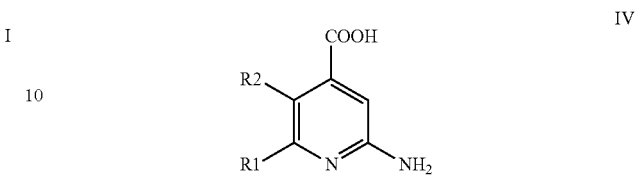

in which R1 and R2 have the meaning as in formula I.

4. The process according to claim 1
in which
R1 is methyl-, ethyl-, iso-propyl-, tert-butyl- or phenyl-;
R2 is H— or methyl-;
or
R1 and R2 together form a —CH$_2$—CH$_2$—CH$_2$— or —CH$_2$—CH$_2$—CH$_2$—CH$_2$— group such that a ring is formed;
R3 is ethyl- or methyl-;
R4 is ethyl- or methyl-.

5. The process according to claim 1
in which
R1 is methyl-, ethyl-, iso-propyl-, tert-butyl- or phenyl- and R2 is H—;
or
R1 is ethyl- and R2 is methyl-;
or
R1 and R2 together form a —CH$_2$—CH$_2$—CH$_2$— group such that a ring is formed;
R3 is ethyl-;
R4 is ethyl-.

6. The process according to claim 1, wherein the reaction comprises NaOEt in EtOH for elimination of water.

7. The process according to claim 2, wherein an inorganic base is used for hydrolysis of the ester groups.

8. The process according to claim 2, wherein NaOH, LiOH, KOH or Ba(OH)$_2$ is used for hydrolysis of the ester groups.

9. The process according to claim 2, wherein the reaction mixture is adjusted to a pH in the range of 5-6 with an acid after hydrolysis of the ester groups.

10. The process according to claim 2, wherein the reaction mixture is adjusted to a pH in the range of 5-6 with hydrochloric acid or H$_2$SO$_4$ after hydrolysis of the ester groups.

11. The process according to claim 3, wherein concentrated H$_2$SO$_4$ is used for decarboxylation.

12. The process according to claim 3, wherein decarboxylation is conducted in the presence of LiCl, NaCl or MgCl$_2$.

13. The process according to claim 3, wherein decarboxylation is conducted at a temperature of 120 to 150° C.

* * * * *